United States Patent [19]

Nortman et al.

[11] Patent Number: 5,334,149
[45] Date of Patent: Aug. 2, 1994

[54] POST-INJECTION SHEATH FOR A HYPODERMIC SYRINGE NEEDLE

[76] Inventors: Marvin Nortman, 119 Plymouth Blvd., Smithtown, N.Y. 11787; Arthur A. Kravets, 464 Old Country Rd., Melville, N.Y. 11747

[21] Appl. No.: 90,874

[22] Filed: Jul. 13, 1993

[51] Int. Cl.[5] .............................................. A61M 5/00
[52] U.S. Cl. .................................. 604/110; 604/198; 604/263
[58] Field of Search ............... 604/110, 187, 192, 198, 604/263, 164

[56] References Cited

U.S. PATENT DOCUMENTS

| | | | |
|---|---|---|---|
| 4,994,041 | 2/1991 | Dombrowski et al. | 604/164 |
| 5,002,533 | 3/1991 | Jullien | 604/110 |
| 5,015,240 | 5/1991 | Soproni et al. | 604/263 X |
| 5,163,908 | 11/1992 | Lambert | 604/110 |

Primary Examiner—John D. Yasko
Attorney, Agent, or Firm—Anderson Kill Olick & Oshinsky

[57] ABSTRACT

A post-injection sheath for a hypodermic syringe needle includes an accordion-shaped resilient sheath body, which is fixedly secured to the needle hub at its one end and is movable from a compressed position, corresponding to a ready-to be used position of the needle, to an expanded position, in which the sheath body covers the needle. The sheath body supports, at its second open end, an end cover which is adapted to pivot from a first position, in which it extends parallel to the longitudinal axis of the sheath body, to a second position, in which it extends transverse to the longitudinal axis of the sheath body and covers the open end of the sheath body. The end cover pivots from its first position to its second position when the sheath body reaches its expanded position. The end cover is provided with a hub portion having a chamber into which the needle tip projects and in which it is deformed.

20 Claims, 2 Drawing Sheets

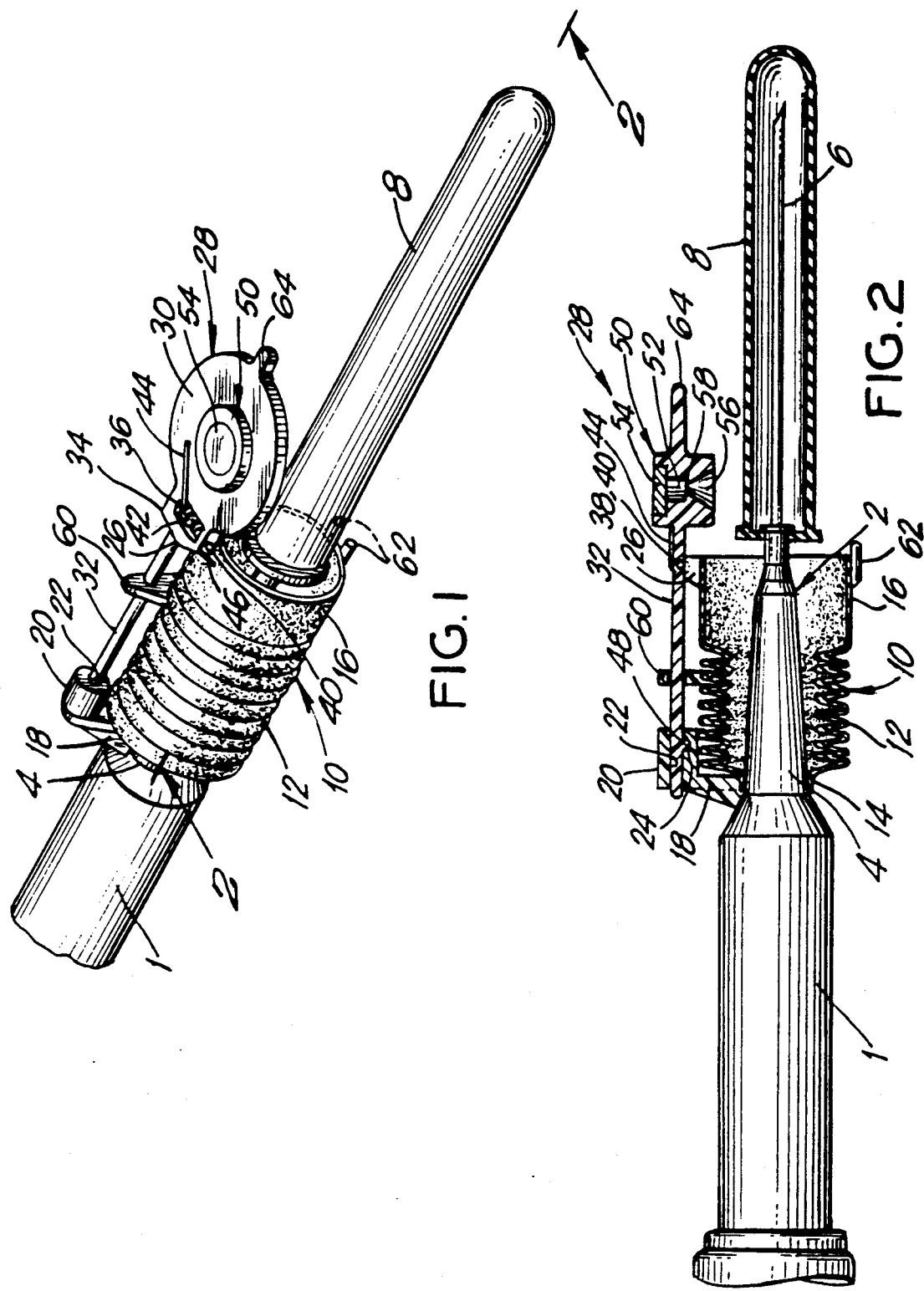

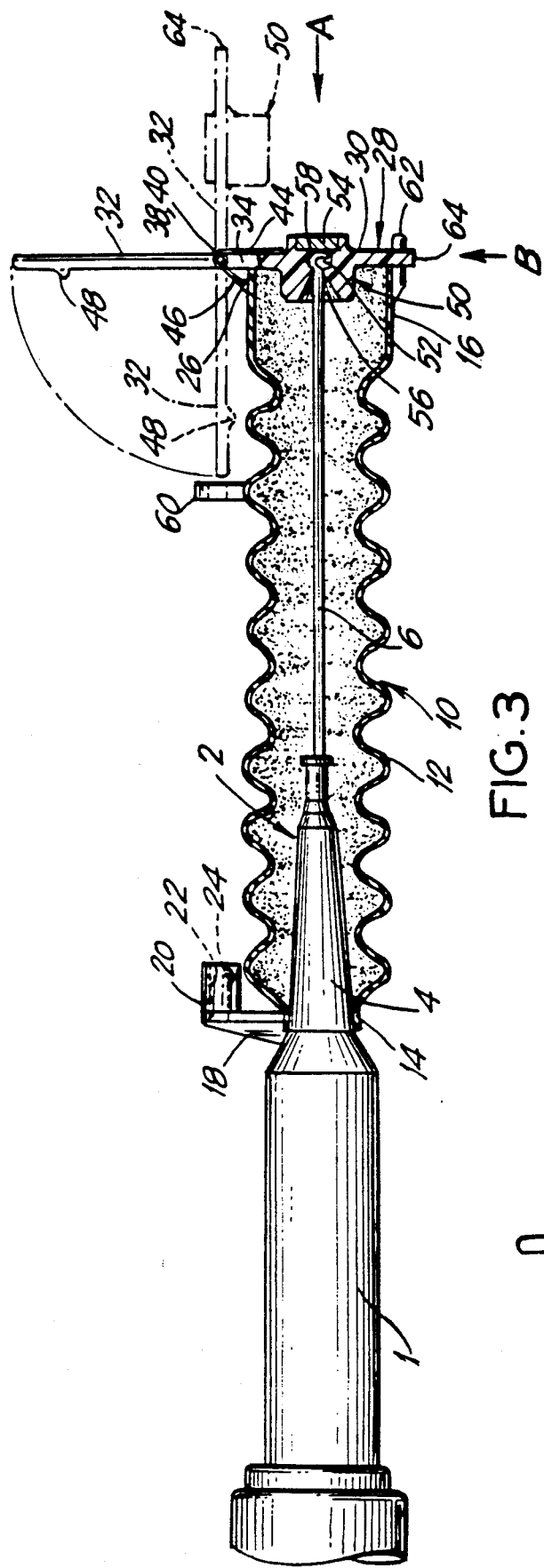
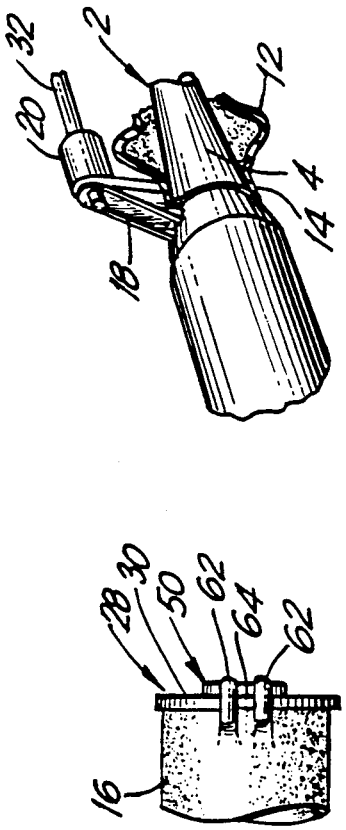
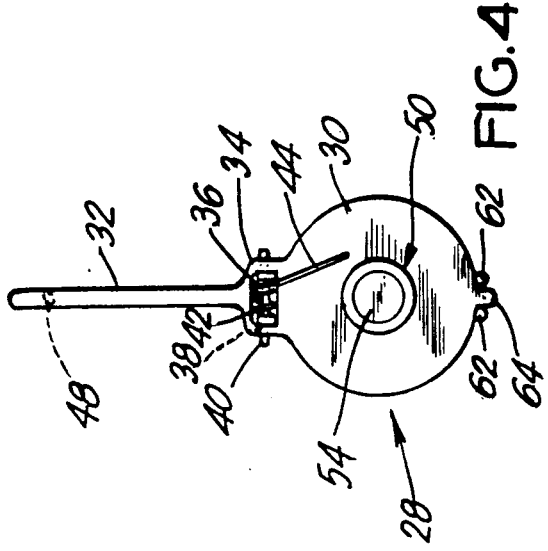

POST-INJECTION SHEATH FOR A HYPODERMIC SYRINGE NEEDLE

BACKGROUND OF THE INVENTION

1. Field of the Invention

The present invention relates to a post-injection needle sheath for a hypodermic syringe needle and more, particularly to a post-injection needle sheath for a hypodermic syringe needle which is easily and conveniently actuated, is self-sealing and simultaneously renders the syringe needle inoperable.

2. Description of the Prior Art

For many years, health care workers, including doctors, nurses, physicians, laboratory personnel and housekeeping personnel of hospitals, doctor's offices and the like were prone to injuries from accidental sticking of the needle into the worker's skin, especially after removal of a needle from a body of a patient and during subsequent disposal of the needle. Such injuries pose grave dangers, particularly if the patient has been exposed to hepatitis and other communicable diseases which can be transmitted by body fluids. The health hazards associated with such injuries became even greater in view of the acquired immune deficiency syndrome (AIDS).

Numerous attempts, including needle protectors, have therefore been made to sheath a syringe needle after its use and to provide for its safe disposal. Needle protectors are generally well known and abound. One such needle protector is disclosed in U.S. Pat. No. 5,015,242. This patent discloses a needle sheath made of a resilient material and having an accordion or bellows shape. The sheath is attached at one of its end to the needle hub. In the "use" position, the needle sheath is compressed and held in its compressed position by an L-shaped bendable retaining element which is also secured to the needle hub. Upon withdrawal of the needle from the body of a patent, the retaining element is bent away, and the sheath expands covering the needle. This construction of a sheath however has numerous drawbacks. It is highly desirable that the protector be actuated with the same hand that holds the syringe, when the needle is withdrawn from the body of a patient, as the other hand is generally used to apply alcohol or other disinfectant to a patient's body. However, it would be difficult to bend away the retaining member with a finger of the same hand used to apply the injection. The finger would have to be inserted between the retaining member and the sheath adjacent to the short leg of the L-shaped retaining member and then, a substantial force must be applied by the finger to bend the retaining member away. Further, even after the sheath covers the needle, nothing prevents the sheath from accidental compression and thus exposure of the needle.

Another type of a post-injection needle sheath is disclosed in U.S. Pat. No. 4,804,371. U.S. Pat. No. 4,804,371 likewise discloses an accordion - or bellows-shaped needle sheath retained in a compressed position during use of the needle. The sheath expands to cover the needle after the needle is withdrawn. This sheath, as the sheath of U.S. Pat. No. 5,015,242, can also be accidentally compressed, exposing the needle.

Yet another post-injection sheath is disclosed in German Offenlegungsschrift DE 38 08 688. The German document discloses a protective cover for a syringe needle, including a resilient sheath attached at one of its ends to the needle hub, with an end cup-shaped member secured to the other end of the sheath. This member has an opening through which the needle extends with the opening being defined by a central tubular portion formed integrally with the end surface of the cup-shaped member. During needle use, the cup-shaped member compresses the sheath and is secured (clamped) to the needle hub. Upon withdrawal of the needle from a stick in the body of a patient, the sheath expands covering the needle. At that point, eccentric or side forces acting on the cup-shaped member displace it relative to the needle axis so that the needle end is located in the space between the circumferential surface of the cup-shaped member and its central tubular portion. To this end, the central tubular portion is formed with an eccentricity relative to the needle axis. However, because the eccentricity is very small (0.2–0.5 mm), the needle would not extend into the guide passage, especially if the production tolerances are taken into account.

SUMMARY OF INVENTION

Accordingly, a main objective of the present invention is to provide a post-injection needle sheath which reliably protects healthcare personnel from a needle stick injury.

Another object of the present invention to provide a post-injection sheath for a hypodermic syringe needle and which is reliable and easy to operate.

A further object of the invention to provide a post-injection needle sheath which can be activated with the same hand that holds the syringe, without affecting handling of the syringe.

These and other objects of the present invention, which will become apparent hereinafter, are achieved by providing a post-injection needle sheath including an accordion-shaped body, secured at its one end to the needle hub and movable from a compressed position in which the needle can be used, to an extended position in which it completely sheathes the needle. The needle sheath, according to the invention, further includes a substantially plate-shaped end cover pivotally supported at its one end on the sheath body end opposite to the end, at which the body is attached to the needle hub. In the compressed position of the sheath body, the end cover extends substantially parallel to the body axis. The sheath includes means, preferably spring means, for pivoting the end cover from its position, in which it extends parallel to the needle axis, to a position in which it extends transverse to the needle axis when the sheath body reaches its extended position. The sheath body has, at its other end, at a location which is diametrically opposite to the location where the end cover is secured to the sheath body, a double ball lock secured to the sheath body for receiving the end of the end cover which is opposite to the end of which the cover is secured to the sheath body. The end cover has, substantially in the middle portion thereof, a hub portion having an inner chamber into which a guide passageway, extending from the inner end surface of the hub portion, opens. When the end cover moves to its transverse position, the end of the needle extends through the passageway into the inner chambers, which is designed in such a manner that the tip of the needle is snared therein so that the end cover is additionally locked to the needle.

The sheath body is retained, in its compressed position, by a retainer arrangement. The sheath actuating mechanism includes a rod which is adapted to be displaced by a thumb and which, upon being acted upon by the thumb, disables the retainer arrangement, so that the compressed sheath body is able to expand either due to its own resiliency or by a spring. The rod displacement also provides for pivoting of the end cover from its position, in which it extends, parallel to the needle axis, to its transverse position.

The above-discussed sheath, as it follows from the foregoing description, can be easily and conveniently actuated. The sheath not only completely encases the needle, but also disables the needle end, so that there's no danger of a needle stick injury to the personnel.

BRIEF DESCRIPTION OF THE DRAWINGS

The objects and features of the present invention will become more apparent and the invention itself will be best understood from the following detailed description of the preferred embodiment, when read with reference to the accompanying drawings, wherein:

FIG. 1 is a perspective view of hypodermic syringe needle with a standard cover and a post-injection sheath according to the present invention;

FIG. 2 is a longitudinal, cross-sectional view of a needle for use with a hypodermic syringe and provided with a post-injection sheath according to the present invention in a shipped position;

FIG. 3 is a cross-sectional view similar to that of FIG. 2, but with the needle in a sheathed position;

FIG. 4 is a view in the direction of arrow "A" in FIG. 3;

FIG. 5 is a view along arrow "B" in FIG. 3; and

FIG. 6 is a view showing the bracket.

DETAILED DESCRIPTION OF THE PREFERRED EMBODIMENT

Referring to the drawings, a needle assembly 2 designated for use with a conventional hypodermic syringe 1, has a hub 4 adapted to be mounted on an end of the conventional hypodermic syringe, and a needle 6 secured to the hub 4. The needle 2, in a non-used condition, is provided with a conventional standard shield 8, which is removed prior to the use of the needle 2, and with a post-injection sheath 10, which is secured to the hub 4 of the needle 2. The sheath 10 comprises an accordion-shaped body 12, which is made of a resilient material, so that the body is able to expand after having been compressed. The body 12 is formed, at its rear end, integrally with a frusto-conical ring member 14, with which the sheath 10 is secured to the hub 4 of the needle 2, e.g., by gluing or other appropriate means. At its front end, the body 12 is formed integrally with a cylindrical ring 16. An annular bracket 18, having a boss 20 on its end surface, is supported on the ring 14 of the sheath body. The bracket 18 can be made integral with the ring 14 or be mounted thereon by gluing or other appropriate means. The boss 20 has a through-opening 22 in which a dimple 24 is formed. Another bracket 26 is fixedly mounted on the front cylindrical ring 16.

The boss 20 of the annular bracket 18 and the bracket 26, support together, in the needle ready-to-be-used position, a one-piece cover 28. The cover 28 is formed of disc-like portion 30, a rod-like member 32, and a substantially rectangular-shaped intermediate portion 34, extending between the rod member 32 and the disc-like portion 30. The intermediate portion 34 has a window 36 into which opposite radial holes 38 open. A pin 40, which is secured in the bracket 26, extends through the holes 38. The pin 40 is designed for supporting a helical spring 42 that biases the cover 28 to a position transverse to the longitudinal axis of the sheath 10. Of course, other types of syringes, e.g., a leaf spring, can also be used. The spring 42 has one leg 44, acting on the outer surface of the disc-like portion 30, with the other leg 46 being supported by the bracket 26.

The rod-like member 32 has, at an end thereof, remote from the portion 30, a boss 48, which, in the use position, engages the dimple 24, thus retaining the sheath body 12 in its compressed position. The end of the rod-like member 32 slightly projects beyond the rear end surface of the boss 20 in this position. During shipment, the sheath assembly may be additionally retained in the compressed position of the sheath body, e.g., by a retaining ring (not shown).

The disc-like portion 30 has a central hub portion 50, having a chamber 52, which is closed from the outer side of the hub portion 50 with a cover member 54 formed of a hard material, e.g., steel or hard plastic material. At its inner side, the hub portion 50 is provided with a frusto-conical passage 56 connected with the chamber 52 by a cylindrical passage 58.

A guide member 60 is provided on the sheath body 12 for supporting the rod-like member 32 of the cover 28. The location of the guide member 60 is so selected that the rear end of the rod-like member 32 clears the guide member 60 in the extended end position of the sheath body 10, so that in that position, the cover 28 pivots to its closing position, in which it closes the open end of the sheath body 12. Intermediate guide member(s) may be provided, if desired, between the boss 20 and the guide member 60. The length of the sheath body 12, the size of the hub portion 50 and location of the cavity 52 are selected so that in the expanded end position of the sheath body 12, the tip of the needle 6 hits the cover member 54, curls and is retained in the chamber 52. As shown in FIG. 3, this eliminates any possibility of a stick injury to the personnel who handles the needle. Locating the needle tip in chamber 52 also insures further retaining of the cover 28 on the open end of the sheath body 12. The sheath body 12 has, at a diametrical end thereof opposite of bracket 26, a lock member 62 for receiving a projection 64 formed at the diametrical end of the portion 30 which is opposite to the rod-like member 32. The lock member 62 may be formed, e.g., as a spring double ball lock in the form of a resilient body at the end of the sheath body 12.

While function of the post-injection sheath according to the invention should be clear from the foregoing description, its function nevertheless will now be described for completeness of the disclosure.

Upon withdrawal of the needle from a needle stick in a body of a patient, the nurse or the physician can immediately push, preferably by the thumb of the hand that holds the syringe, the end of the rod-like men, her 32 to displace the boss 48 at the end of the rod-like member 32 from the dimple 24 in the boss 20. As soon as the boss 48 clears the dimple 24, the sheath body 12 expands by its innate resiliency and will cover the needle 6. At the end position of the sheath body 12, the end of the rod-like member 32 will clear the guide member 60, as shown in dashed lines in FIG. 3 and the spring 42 will cause pivoting of the cover 28 to its closed position, with the cover 28 being locked in this position by engagement of the projection 64 in the lock member 62. Simultaneously with locking of the cover 28 in its closed position, the needle tip will be curled and snared in the chamber 62.

As it follows from the foregoing description, the present invention provides a post-injection sheath that perfectly sheathes a used needle, and thus prevents the personnel that handles the used needle from any stick injury.

While the present invention has been shown and described with reference to the presently preferred embodiment of the invention, various modification thereof will be apparent to those skilled in the art and, therefore, it is not intended that the invention be limited to the disclosed embodiment or to the details thereof and departures may be made therefrom within the spirit and scope of the invention as defined in the appended claims.

What is claimed is:

1. A post-injection sheath for a hypodermic syringe needle having a hub, said post-injection sheath comprising:
   an accordion-shaped resilient sheath body having a first end, at which it is fixedly secured to the needle hub, and a second open end, said sheath body having a compressed position, which corresponds to a ready-to be-used position of the needle, and an expanded position, in which it covers the needle;
   an end cover pivotally supported on said sheath body at said second open end for closing said second open end in the expanded position of said sheath body, said end cover having a first position, in which it extends substantially parallel to a longitudinal axis of said sheath body, and a second position, in which it extends transverse to the longitudinal axis of said sheath body and covers said open end;
   means for pivotally supporting said end cover at said second open end of said sheath body;
   means for automatically pivoting said end cover from the first position thereof to the second position thereof in the expanded position of said sheath body; and
   means for retaining said sheath body in the compressed position thereof, wherein said retaining means are adapted to be manually disabled, and said sheath body automatically moves to the expanded position thereof upon disabling of said retaining means.

2. A post-injection sheath as set forth in claim 1, further comprising a lock means secured to said sheath body at said second open end, at a location which is diametrically opposite to a location at which said end cover is secured to said sheath body, for locking said end cover in the second position thereof.

3. A post-injection sheath as set forth in claim 1, wherein said end cover has a disc-like portion, a rod-like member and a substantially rectangularly-shaped intermediate portion, extending between said rod-like member and said disc-like portion,
   wherein said intermediate portion has a window and radial hole means opening into said window,
   wherein said supporting means comprises a bracket fixedly secured at said second open end of said sheath body, and a pin supported by said bracket and extending through said radial hole means and bridging said window, and
   wherein said pivoting means comprises a spring supported on said pin.

4. A post-injection sheath as set forth in claim 3, wherein said disc-like portion has a hub portion having a chamber with a bottom formed of a hard material and passage means connecting an inner end surface of said hub portion with said chamber,
   wherein lengths of said sheath body and said passage means and dimensions of said chamber are so selected that, upon closing of said second open end of said sheath body with said cover, the needle tip is curled by the bottom of said chamber and is completely entrapped in said chamber.

5. A post-injection sheath as set forth in claim 3, wherein said retaining means comprises a bracket fixedly secured at said first end of said sheath body and having a boss member formed integrally therewith
   wherein said boss member has a through-bore and a dimple formed in said bore, and
   wherein said rod-like member extends through said through-bore and has a free end projecting beyond an end surface of said boss member, and a boss at said free end engaging said dimple for retaining the sheath body in the compressed position thereof, said sheath body being movable from the compressed position thereof to the extended position thereof upon manually pressing at said free end of said rod-like member to disengage said boss from said dimple.

6. A post-injection sheath as set forth in claim 5, further comprising a guide fixedly secured to said sheath body for guiding said rod-like member during movement of said sheath body from the compressed position thereof to the expanded position thereof,
   wherein a location of said guide on said sheath body is so selected that free end of said rod-like member clears said guide member when said sheath body reaches the expanded position thereof, wherein said spring pivots said end cover into the second position of said end cover.

7. A post-injection sheath as set forth in claim 1, wherein said end cover includes means for rendering the needle inoperable in the second position of said end cover.

8. A post-injection sheath for a hypodermic syringe needle having a hub and a tip, said post-injection sheath comprising:
   an accordion-shaped resilient sheath body having a first end, at which it is fixedly secured to the needle hub, and a second open end, said sheath body having a compressed position which corresponds to a ready-to be-used position of the needle, and an expanded position, in which it covers the needle; and
   an end cover, pivotally supported on said sheath body at said second open end for closing said second open end in the expanded position of said sheath body, said cover having a first position, in which it extends substantially parallel to a longitudinal axis of said sheath body, and a second position, in which it extends transverse to the longitudinal axis of said sheath body and covers said open end; and
   means formed integrally with said end cover for deforming the needle tip and attaching said end cover to said needle.

9. A post-injection sheath as set forth in claim 8, further comprising:
   means for pivotally supporting said end cover at said open end of said sheath body;
   means for automatically pivoting said end cover from the first position thereof to the second position thereof in the expanded position of said sheath body; and manually actuatable means for retaining said sheath body in the compressed position thereof.

10. A post-injection sheath, as set forth in claim 9, wherein said end cover has a disc-like portion for covering said open end of said sheath body, and said deforming means comprises a hub portion formed integrally with said disc-like portion and having a chamber with a bottom formed of a hard material, and passage means connecting an inner end surface of said hub portion with said chamber.

11. A post-injection sheath, as set forth in claim 10, wherein said end cover further includes a rod-like member and a substantially rectangularly-shaped intermediate portion, extending between said rod-like member and said disc-like portion:

wherein said intermediate portion has a window and radial hole means opening into said window;

wherein said supporting means comprises a bracket, fixedly secured at said second open end of said sheath body, and a pin supported by said bracket and extending through said radial hole means and bridging said window; and wherein said pivoting means comprises a spring supported on said pin.

12. A hypodermic syringe assembly comprising:
a hypodermic syringe;
a needle attachable to said syringe and having a hub and tip; and
a post-injection sheath attachable to said needle hub, wherein said post-injection sheath comprises:
an accordion-shaped, resilient sheath body having a first end, at which it is fixedly secured to the needle hub, and a second open end, said sheath body having a compressed position which corresponds to a ready-to be-used position of the needle, and an expanded position, in which it covers the needle;
an end cover pivotally supported on said sheath body at said second open end for closing said second open end in the expanded position of said sheath body, said end cover having a first position, in which it extends substantially parallel to a longitudinal axis of said sheath body, and a second position, in which it extends transverse to the longitudinal axis of said sheath body and covers said open end;
means for pivotally supporting said end cover at said second open end of said sheath body;
means for automatically pivoting said end cover from the first position thereof to the second position thereof in the expanded position of said sheath body; and
means for retaining said sheath body in the compressed position thereof, wherein said retaining means are adapted to be manually disabled and said sheath body automatically moves to the expanded position thereof upon disabling of said retaining means.

13. A hypodermic syringe assembly as set forth in claim 12, further comprising lock means secured to said sheath body at said second open end at a location, which is diametrically opposite to a location at which said end cover is secured to said sheath body, for locking said end cover in the second position thereof.

14. A hypodermic syringe assembly as set forth in claim 12, wherein said end cover has a disc-like portion, a rod-like member and a substantially rectangularly-shaped intermediate portion, extending between said rod-like member and said disc-like portion;

wherein said intermediate portion has a window and radial hole means opening into said window;

wherein said supporting means comprises a bracket fixedly secured at said second open end of said sheath body and a pin supported by said bracket and extending through said radial hole means and bridging said window; and wherein said pivoting means comprises a spring supported on said pin.

15. A hypodermic syringe assembly, as set forth in claim 14, wherein said disc-like portion has a hub portion having a chamber with a bottom formed of a hard material and passage means connecting an inner end surface of said hub portion with said chamber;

wherein lengths of said sheath body and said passage means and dimensions of said chamber are so selected that, upon closing of said second open end of said sheath body with said cover, the needle tip is curled by the bottom of said chamber and is completely entrapped in said chamber.

16. A hypodermic syringe assembly, comprising:
a hypodermic syringe;
a needle attachable to said syringe and having a hub and a tip; and
a post-injection sheath attachable to said needle hub, wherein said-post-injection sheath, comprises:
an accordion-shaped resilient sheath body having a first end, at which it is fixedly secured to the needle hub, and a second open end, said sheath body having a compressed position, which corresponds to a ready-to be-used position of the needle, and an expanded position, in which it covers the needle;
an end cover pivotally supported on said sheath body at said second open end for closing said second open end in the expanded position of said sheath body, said end cover having a first position, in which it extends substantially parallel to a longitudinal axis of said sheath body, and a second position, in which it extends transverse to the longitudinal axis of said sheath body and covers said open end; and
means formed integrally with said end cover for deforming the needle tip and attaching said end cover to said needle.

17. A hypodermic syringe assembly as set forth in claim 16, further comprising:
means for pivotally supporting said end cover at said second open end of said sheath body;
means for automatically pivoting said end cover from the first position thereof to the second position thereof in the expanded position of said sheath body; and
means for retaining said sheath body in the compressed position thereof, wherein said retaining means are adapted to be manually disabled and said sheath body automatically moves to the expanded position thereof upon disabling of said retaining means.

18. A hypodermic syringe assembly as set forth in claim 16, wherein said end cover has a disc-like portion for covering said open end of said sheath body and said deforming means comprises a hub portion formed integrally with said disc-like portion and having a chamber with a bottom formed of a hard material and passage means connecting an inner end surface of said hub portion with said chamber; and wherein lengths of said sheath body and said passage means and dimensions of said chamber are so selected that, upon closing of said second open end of said sheath body, with said cover, the needle tip is curled by the bottom of said chamber and is completely entrapped in said chamber.

19. A post-injection sheath for a hypodermic syringe needle having a hub, said post-injection sheath comprising:

an accordion-shaped resilient sheath body having a first end, at which it is fixedly secured to the needle hub, and a second open end, said sheath body having a compressed position, which corresponds to a ready-to be-used position of the needle, and an expanded position, in which it covers the needle;

an end cover supported on said sheath body at said second open end for closing said second open end in the expanded position of said sheath body, said end cover having a first position, in which it does not obstruct use of the needle, and a second position, in which it extends transverse to a longitudinal axis of said sheath body and covers said open end;

means for supporting said end cover at said second open end of said sheath body in the first position of said end cover;

means for retaining said sheath body in the compressed position thereof, wherein said retaining means are adapted to be manually disabled, and said sheath body automatically moves to the expanded position thereof upon disabling of said retaining means; and means for moving said end cover from the first position thereof to the second position thereof when said sheath body reaches the expanded position thereof.

20. A hypodermic syringe assembly, comprising:

a hypodermic syringe;

a needle attachable to said syringe and having a hub and a tip; and a post-injection sheath attachable to said needle hub, wherein said post-injection sheath comprises:

an accordion-shaped resilient sheath body having a first end, at which it is fixedly secured to the needle hub, and a second open end, said sheath body having a compressed position, which corresponds to a ready-to be-used position of the needle, and an expanded position, in which it covers the needle;

an end cover supported on said sheath body at said second open end for closing said second open end in the expanded position of said sheath body, said end cover having a first position, in which it does not obstruct use of the needle, and a second position, in which it extends transverse to a longitudinal axis of said sheath body and covers said open end;

means for supporting said end cover at said second open end of said sheath body in the first position of said end cover;

means for retaining said sheath body in the compressed position thereof, wherein said retaining means are adapted to be manually disabled, and said sheath body automatically moves to the expanded position thereof upon disabling of said retaining means; and means for moving said end cover from the first position thereof to the second position thereof when said sheath body reaches the expanded position thereof.

* * * * *